(12) United States Patent
Calvert

(10) Patent No.: US 8,991,019 B1
(45) Date of Patent: Mar. 31, 2015

(54) CRIME-SCENE BODY BAG

(71) Applicant: CSBB Associates, Trustee for Crime-scene body bag CRT Trust, Manassas, VA (US)

(72) Inventor: S. Mill Calvert, Manassas, VA (US)

(73) Assignee: CSBB Associates, Trustee for Crime-scene body bag CRT Trust, Manassas, VA (US)

( * ) Notice: Subject to any disclaimer, the term of this patent is extended or adjusted under 35 U.S.C. 154(b) by 0 days.

(21) Appl. No.: 14/478,914

(22) Filed: Sep. 5, 2014

(51) Int. Cl.
*A61G 17/06* (2006.01)
*G06K 9/00* (2006.01)
*B65D 33/06* (2006.01)
*B65D 33/25* (2006.01)

(52) U.S. Cl.
CPC ............ *A61G 17/06* (2013.01); *G06K 9/00006* (2013.01); *B65D 33/065* (2013.01); *B65D 33/2508* (2013.01)
USPC ........................................................... 27/28

(58) Field of Classification Search
CPC ... A61G 17/00; A61G 17/06; A61G 2017/00; G06K 9/00006; B65D 31/14; B65D 33/065; B65D 33/2508; B65D 33/2591; G06F 1/1628
USPC ............. 27/28; 383/16, 64, 66, 100; 382/124; 361/679.26, 679.55; 340/693.5
See application file for complete search history.

(56) References Cited

U.S. PATENT DOCUMENTS

| | | | |
|---|---|---|---|
| 4,790,051 A | 12/1988 | Knight | |
| 5,659,933 A * | 8/1997 | McWilliams | 27/28 |
| 7,228,603 B2 * | 6/2007 | Craig | 27/28 |
| 7,337,511 B2 * | 3/2008 | Yu et al. | 27/28 |
| 7,496,995 B2 * | 3/2009 | Rosario et al. | 27/28 |
| 2009/0007402 A1 * | 1/2009 | Carroll et al. | 27/28 |
| 2010/0018088 A1 * | 1/2010 | Rajpal | 40/5 |
| 2010/0315772 A1 * | 12/2010 | Ko | 361/679.55 |
| 2014/0259577 A1 * | 9/2014 | Richardson | 27/28 |

\* cited by examiner

*Primary Examiner* — William Miller
(74) *Attorney, Agent, or Firm* — Louis Ventre, Jr.

(57) ABSTRACT

A crime-scene body bag is made with a flexible material forming an enclosure defining an interior chamber sufficient to accommodate the remains of a deceased person. The bag is opened and closed with a zippering mechanism. A platform is embedded into the flexible material containing a variety of components including an electronic data storage unit; a fingerprint scanner, a digital voice recorder, a camera, a nozzle for insertion of a cover gas and for release of gases within the enclosure, a global positioning system monitor, a display screen, and a radio-frequency identification tag. Optional components include a pressurized gas capsule, an odor absorbing compound, an anti-bacterial agent, a sensor recording when the zipper is opened and the location, a bio-medical scanner, a radiation dosimeter, a locking mechanism, an end-lift handle, a central lifting strap, a zippered pouch, and a vacuum attachment.

12 Claims, 2 Drawing Sheets

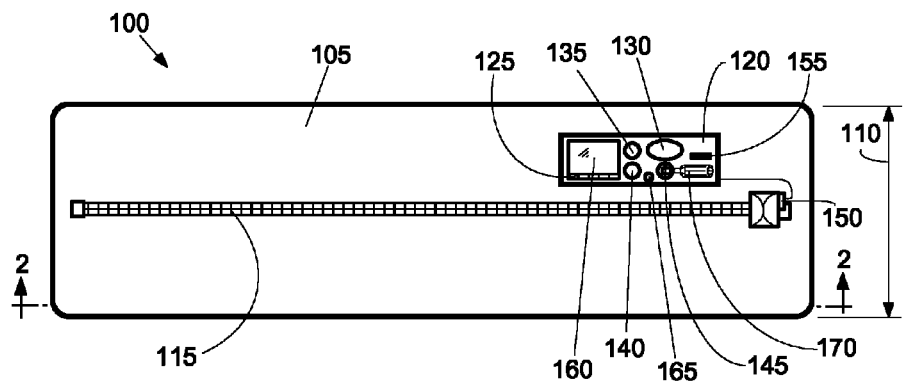
FIG.1
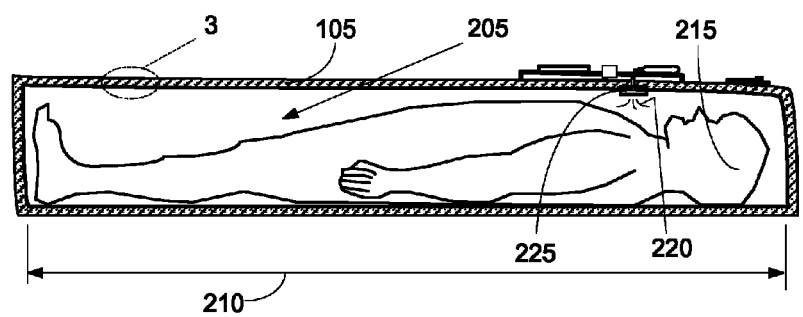
FIG.2
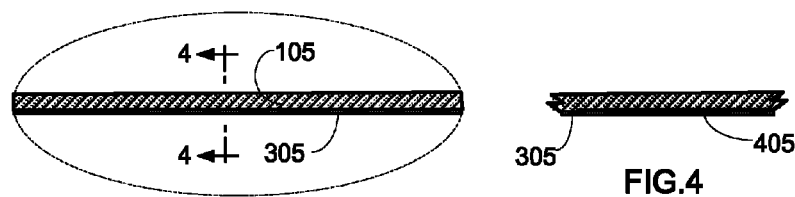
FIG.3
FIG.4

CRIME-SCENE BODY BAG

TECHNICAL FIELD

In the field of flexible bags, a body bag having an embedded component platform and other features that provide added functionality associated with crime scene investigation and the storage, transportation and evaluation of a cadaver.

BACKGROUND ART

Prior art for body bags concentrates on packaging, transporting and storing the remains. Body bags have not been a tool to assist in forensic analysis, taking fingerprints of the corpse, recording of the scene, preservation of observations, or chain of custody proofs.

A death investigator arriving at a crime scene will first confirm the death and conduct a scene walk through. Having a body bag that can also serve as a recording device for pertinent scene-walk-through observations and for coroner interactions with officials at the site can serve an important function in criminal investigation. For instance, the death investigator will typically identify the first responder to ascertain if any artifacts or contamination may have been introduced to the death scene. Audio recording of this interaction will create a subsequently reviewable record.

Existing tools for recovering fingerprints include brushes, powders, tape, chemicals, lift cards, a magnifying glass and Super Glue. Body bags having a fingerprint scanner that saves a cadaver's prints to an embedded hard drive are not known. Also, a body bag with an integral high definition camera can photograph and centrally store other discovered fingerprints made visible by these existing tools. Such a camera could also record and centrally store crime scene conditions, such as blood spatter patterns, which can reveal the type of weapon that was used.

Federal regulations deem all bodily fluids to be biohazards, so any blood or tissue at a crime scene is considered a potential source of infection. Existing body bags offer containment for such biohazards. If the victim is dead and there is blood on the body, the investigator will collect a blood sample either by submitting a piece of clothing or by using a sterile cloth square and a small amount of distilled water to remove some blood from the body. A body bag that also doubles as a means to record and centrally store the oral descriptions of where and when such samples are taken is an aid to documenting the conditions incident to such collection.

Once a body bag is zipped up, it can be unzipped for a number of reasons, such as for identification by the next of kin. Currently, there is no inherent means to automatically catalog the opening of the body bag or for recording the reasons for such action or the results of such action. A body bag that can store the time and date and also record the oral statements and video made when the bag is opened provides a heretofore missing ability to supplement and store identification information and chain of custody activities on the remains.

SUMMARY OF INVENTION

A crime-scene body bag is made with a flexible material forming an enclosure defining an interior chamber sufficient to accommodate the remains of a deceased person. The bag is opened and closed with a zippering mechanism. A platform is embedded into the flexible material containing a variety of components including an electronic data storage unit; a fingerprint scanner, a digital voice recorder, a camera, a nozzle for insertion of a cover gas and for release of gases within the enclosure, a global positioning system monitor, a display screen, and a radio-frequency identification tag. Optional components and features include a pressurized gas capsule holding the cover gas, an odor absorbing compound within the interior chamber, an anti-bacterial agent within the interior chamber, a sensor recording when the zipper is opened and the location of the crime-scene body bag when the zipper is opened, a bio-medical scanner, a radiation dosimeter, a locking mechanism, an end-lift handle, a central lifting strap, a zippered pouch, and a vacuum attachment to suck out any gases within.

Technical Problem

There is presently no body bag that serves a data storage function for the output of interconnected forensic instruments integrated into the body bag.

In mankind's journey through life, the physical death of our body is, of course, a part of life. Since the earliest days of man's existence on earth, mankind has used the technology of putting the deceased body into a bag to cover it for moving it or burial. Over many thousands of years about the only technological improvement in body bags has been the use of a plastic body bag instead of one made from cloth or fiber. Why is it that in our high-technology world of computer networks and landing probes on Mars, the technology of the body bag has been overlooked. It is probably because most people, or inventors, don't like to think about our own physical mortality.

Solution to Problem

The solution is a crime-scene body bag that incorporates and integrates high technology forensic instruments and provides important chain of custody information. The forensic instruments are connected together and either automatically or manually store readings or recordings to a unified central data storage medium. Since the instruments are permanently affixed or embedded within the crime-scene body bag, they cannot be lost or misplaced.

Advantageous Effects of Invention

The features of the crime-scene body bag will prevent the spread of infectious diseases and toxins, will help to identify causes of death, will help both coroners and law enforcement officers to better do their jobs, will help to document and present evidence for criminal or war crime trials, will provide online links to network law enforcement computer network, will help to locate and identify missing and exploited children, will greatly help in the war on terror and other mass casualty events, and will do many other beneficial things when it comes to dealing with deceased bodies.

The invention of the crime-scene body bag has now moved us into the space-age high technology environment that we live in. No longer will we use the same antiquated body bag technology that has been used for thousands of years.

The front of the crime-scene body bag has a high-tech computer and optionally a bio medical scanner on the front. The crime-scene body bag comes folded up in a package that is about the size of a computer laptop. Before unwrapping and unfolding the bag, it can be held to start recording information from the death scene.

The crime-scene body bag has a camera that preferably may take both moving and still pictures of the death scene, while a digital voice recorder may record all comments by the personnel on the scene. A finger of the deceased can be placed on the unit to make a fingerprint scan of the deceased.

The crime-scene body bag also preferably uses the bio medical scanner to sense the presence of deoxyribonucleic acid (DNA) and perform computer-assisted blood analysis to look for drugs, poisons, infectious diseases, anthrax, Ebola, and other chemical agents.

The crime-scene body bag may also have a radiation dosimeter badge to alert for any dirty bomb or radiation danger. When the body bag is delivered to the morgue, the computer unit will be able to tie in with the medical examiner's computer system and other government and law enforcement computer networks, such as National Crime Information Center (NCIC), as well as the National Security Agency (NSA) and Federal Bureau of Investigation (FBI) fingerprint database. This will help evidence to be located and shared and will help to solve many crimes.

The entire inside of the crime-scene body bag is preferably coated with a smell absorbing compound that also has anti-bacterial agents. When the bag is shut, preferably with an airtight zipper, the bag has a nozzle to spray in anti-bacterial and preservative gases.

The zipper tab may engage a locking bar so no one can interfere with the body or evidence. When the coroner wants to open the bag at the morgue, there is preferably a vacuum attachment so he can hook on a medical suction vacuum and suck out the contaminated air upon opening the bag.

The outside of the bag preferably has lift handles on the top and bottom and can also have a central lift strap in case the bag needs to be hoisted up.

The top of the outside of the bag also preferably has a personal effects zippered pouch to store things that the deceased had with him, such as wallet, identification, phone, death scene evidence, and other miscellaneous items.

The invention of the crime-scene body bag will bring quite a number of needed technologies to the issue of dealing with corpses. It will be of great benefit to government, law enforcement, medical examiners, military, disease control officials, lawyers involved in litigation, health departments, doctors and families that have lost someone.

BRIEF DESCRIPTION OF DRAWINGS

The drawings illustrate preferred embodiments of the crime-scene body bag according to the disclosure. The reference numbers in the drawings are used consistently throughout. New reference numbers in FIG. 2 are given the 200 series numbers. Similarly, new reference numbers in each succeeding drawing are given a corresponding series number beginning with the figure number.

FIG. 1 is a top view of a crime-scene body bag.

FIG. 2 is a sectional view along cut 2-2 of FIG. 1.

FIG. 3 is a portion of a view in FIG. 1 enlarged for magnification purposes.

FIG. 4 is a sectional view along cut 4-4 of FIG. 3.

DESCRIPTION OF EMBODIMENTS

Figure 5:
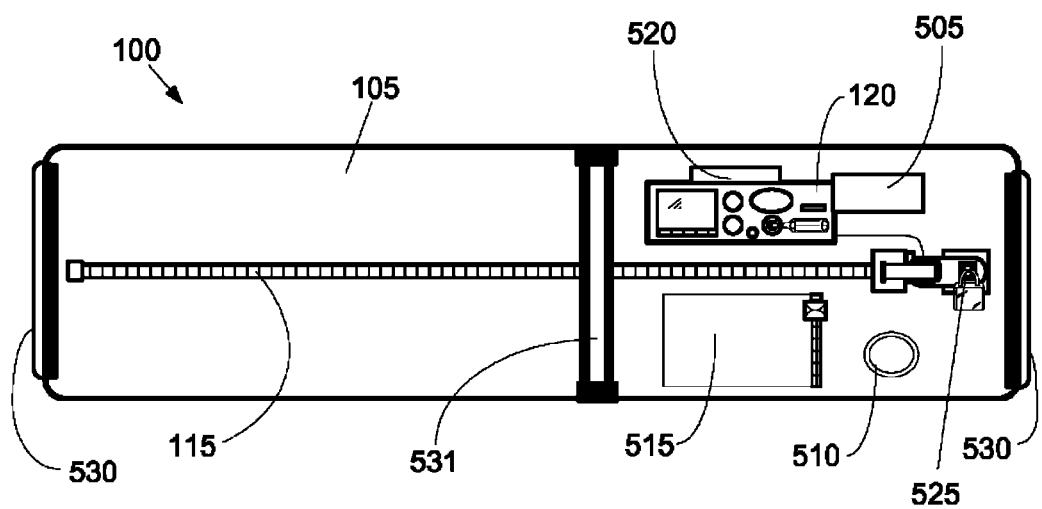
FIG. 5 is a top view of an alternative embodiment of a crime-scene body bag.

In the following description, reference is made to the accompanying drawings, which form a part hereof and which illustrate several embodiments of the present invention. The drawings and the preferred embodiments of the invention are presented with the understanding that the present invention is susceptible of embodiments in many different forms and, therefore, other embodiments may be utilized and structural, and operational changes may be made without departing from the scope of the present invention.

FIG. 1 illustrates a preferred embodiment of a crime-scene body bag (100) according to the disclosure herein. The crime-scene body bag (100) is essentially a person-sized zippered bag made of a flexible material (105) such as plastic and a platform (120), which is a mounting mechanism for a computerized set of interconnected instruments. Examples of a suitable plastic material include a polyolefin, nylon and polyvinyl sheet materials, particularly polyolefin materials such as polyethylene or polypropylene. The flexible material (105) may be reinforced with strands of fiber or metal.

Thus, the crime-scene body bag (100) includes the flexible material (105) forming an enclosure, the enclosure defining an interior chamber (205) having an axial length (210) and a width (110) sufficient to accommodate remains (215) of a deceased person.

The enclosure includes a zippering mechanism (115) for opening and closing the enclosure. The zippering mechanism (115) extends along the axial length (210) of the enclosure to enable placement of the remains (215) of the deceased person in the enclosure. The zippering mechanism (115) is essentially an "access device" such as standard zipper or a rib-in-groove closure. Preferably, the zippering mechanism (115) seals the enclosure to contain any decomposition gases and liquids.

The platform (120) is adhered to, preferably by embedding into, the flexible material (105). The platform (120) preferably includes forensic instruments or components mounted thereto and integrated via a central processing unit or computer.

A first preferred component of the platform (120) is a non-transitory computer readable storage device (125). This is a physical storage device readable by a machine. The computer readable storage device (125) can store data that is accessible by a computer. The computer readable storage device (125) is preferably a non-removable hard drive, but may include a backup Universal Serial Bus (USB) flash drive that can be easily removed and physically transferred to a computer. Other examples include devices such as a magnetic cassette, a flash memory card, a digital video disk, a compact disc, an optical disc, a Bernoulli cartridge, a random access memory (RAM) card, read only memory (ROM) card, and other such storage devices.

A second preferred component of the platform (120) is a fingerprint scanner (130) able to store fingerprint data on the non-transitory computer readable storage device (125). The fingerprint scanner (130) is, for example, an optical scanner or a capacitance scanner, which are known.

An optical scanner is a charge coupled device (CCD). A CCD is an array of light-sensitive diodes called photosites. The photosites generate an electrical signal in response to light. Each photosite records a pixel representing the light that hit that photosite. Collectively, the light and dark pixels form an image of the scanned fingerprint.

A capacitive scanner generates an image of the ridges and valleys that make up a fingerprint. The capacitors use electrical current to sense the fingerprint. The capacitive scanner uses a sensor made up of one or more semiconductor chips containing an array of cells. Each cell includes two conductor plates, covered with an insulating layer. The cells are usually smaller than the width of one fingerprint ridge on a finger. The sensor is connected to an integrator, an electrical circuit built around an inverting amplifier. The inverting amplifier is a complex semiconductor device, made up of a number of transistors, resistors and capacitors.

A third preferred component of the platform (120) is a digital voice recorder (135), which is able to store audio entries as data on the non-transitory computer readable storage device (125). The digital voice recorder (135) is preferably a battery operated device able to record audio files. Various recording formats are available, the most common being files having an extension such as WAV, WMA, MP3, DSS or DS2. The electronic audio file stored in the non-transitory computer readable storage device (125) can be transferred electronically, e.g. via WAN, LAN, USB, e-mail, telephony, or other available transfer means.

A fourth preferred component of the platform (120) is a camera (140) able to store images, including still photos and movies, as data on the non-transitory computer readable storage device (125). The camera is preferably a CMOS active pixel sensor "camera-on-a-chip." This is a small unit, typically having plastic aspheric lens elements made with varying dispersion and refractive indexes. The camera (140) preferably applies distortion optics, vignetting, and various optical aberration corrections to the image. Preferably, the image is then compressed into a suitable format. Examples of common suitable formats include jpeg and tiff formats for a photo and MPG-2 or advanced video codec high definition (AVCHD) formats for a movie. The compressed file is then stored on the non-transitory computer readable storage device (125). An alternative embodiment uses a camera with CCD sensors.

A fifth preferred component of the platform (120) is a nozzle (145) connected to the interior of the bag to enable insertion of a cover gas (220). The nozzle (145) is further connected to a sensor (150) that prevents cover gas (220) insertion when the zippering mechanism (115) is open. The nozzle (145) includes a release valve (225) that releases gases within the enclosure when over-pressurization occurs.

A sixth preferred component of the platform (120) is a global positioning system monitor (155) able to transfer location information from the global positioning system monitor (155) to a requesting computer. The global positioning system monitor (155) has a receiver that communicates with one or more of the global positioning satellites in the global positioning (GPS) system. The built-in receiver typically trilaterates its position using data from at least three GPS satellites and the receiver. The global positioning system monitor (155) preferably determines its location by performing a calculation based on the intersecting point of overlapping spheres determined by the satellites and the receiver in the global positioning system monitor (155).

A seventh preferred component of the platform (120) is a screen (160) that enables a user to view and access the data in the non-transitory computer readable storage device (125). The screen (160) is also generally referred to as a video screen, which is the portion of a computer on which information is displayed. The screen (160) is preferably a standard flat-panel LCD screen. As is typical, it is preferred that the screen (160) is backlit to make it easier to read in bright environments. The screen (160) is preferably a touch screen that also enables a user to interact the components on the platform (120) and the data stored in the non-transitory computer readable storage device (125) by touching areas on the screen (160). Such interaction is enabled by the computer, which is preferably a microprocessor. The computer controls the components of the platform (120).

An eighth preferred component of the platform (120) is a radio-frequency identification tag (165) responsive to radio-frequency queries. The radio-frequency identification tag (165) operates wirelessly employing electromagnetic fields to transfer data. Such operability is enabled by the radio-frequency identification tag (165), which is part of the platform (120) either as an attachment or built into the structure of the platform.

The radio-frequency identification tag (165) contains electronically stored information about the crime-scene body bag (100). The radio-frequency identification tag (165) transfers that stored information when queried by an electromagnetic field or radio signal. The radio-frequency identification tag (165) is preferably a passive transponder to emit microwaves or UHF radio waves upon request of an interrogating signal. The radio-frequency identification tag (165) uses an electronic chip, preferably applied to a substrate to form a label that is affixed to the platform (120).

In one embodiment, the radio-frequency identification tag (165) is powered by collecting energy from the interrogating electromagnetic field. In this embodiment, the radio-frequency identification tag (165) is read at a short range of a few meters using electromagnetic induction by an electromagnetic field.

In an alternative embodiment, the radio-frequency identification tag (165) has a range of hundreds of meters enabled by drawing power from a battery, such as a battery supporting operation of the components on the platform (120).

The crime-scene body bag (100) may include a pressurized gas capsule (170) attached to the platform (120). The pressurized gas capsule (170) is preferably a typical gas cartridge often described as a thumb-size metal container. It preferably holds a noble or an inert gas, called a cover gas (220), which will not react with the remains (215) within the crime-scene body bag (100). Exemplary gases for this application include carbon dioxide, nitrogen, argon, or other noble gas. The pressurized gas capsule (170) is connected to the nozzle (145) so as to permit injection of the cover gas (220) stored within the pressurized gas capsule (170) over the remains (215) within the enclosure.

The crime-scene body bag (100) may include an odor absorbing compound (305) within the interior chamber (205). The odor absorbing compound (305) functions to absorb, mask or mitigate odors emanating from the remains (215).

The odor absorbing compound (305) is preferably a coating on the inner surface of the bag, as shown in FIG. 3. The coating may be in stripes of limited area as shown in FIG. 4, or spread out over the entire inner surface. Operability may be enhanced by a plastic covering over the coating where the plastic covering is peeled off when activation of the odor absorbing compound (305) is desired.

Alternative embodiments employ a separate packet of odor absorbing compound, such as for example, a solid odor absorbing compound within a porous bag that may be placed within the crime-scene body bag (100) if desired and removed when not wanted.

Exemplary odor absorbing compounds include activated carbon, silica, alumina, titania, clay, zinc ricinoleate and magnesia. The odor absorbing compound (305) may include a complexing agent or an encapsulating agent, such as carbohydrates, cyclodextrins, gums, lipids, celluloses, silicates, clays, synthetic polymers, hydrogel particles, superabsorbent polymer particles, desiccant particles, cyclodextrin particles, and synthetic polymer particles.

The crime-scene body bag (100) may include an anti-bacterial agent (405) within the interior chamber (205). The anti-bacterial agent (405) is preferably one that releases a steady gaseous chemical, such as chlorine dioxide, known as an antimicrobial substance. In one embodiment, the anti-bacterial agent (405) is preferably a coating on the inner surface of the bag, as shown in FIG. 3. The anti-bacterial agent (405) may be in stripes of limited area, or spread out over the entire inner surface. FIG. 4 shows alternating stripes of the odor absorbing compound (305) and the anti-bacterial agent (405) for illustration purposes only. The actual distribution of either the anti-bacterial agent (405) or the odor absorbing compound (305) may have any practical arrangement.

Operability may be enhanced by a plastic covering over the coating where the plastic covering is peeled off when release of the anti-bacterial agent (405) is desired. Alternative embodiments employ a separate packet of anti-bacterial agent (405) that can be activated when needed and not employed when unneeded.

Confidence in the security of the remains (215) in the crime-scene body bag (100) and also evidence of chain of custody may be enhanced by connecting the sensor (150) to the non-transitory computer readable storage device (125) to record data identifying when the zipper is opened or closed. For example, time and date information can be obtained from a system clock or from an internet or wi-fi connection and stored to record the opening and closing event. This sensor (150), working in combination with the global positioning system monitor (155), may also be set to store the location of the crime-scene body bag (100) when the zipper is opened or closed. The sensor (150) may preferably be set to automatically turn on, for example for a pre-determined period of time, the audio recorder and/or the camera, so that events and conversation between the opening and closing of the crime-scene body bag (100) will also be recorded.

The crime-scene body bag (100) may include a bio-medical scanner (505) that outputs data to the non-transitory computer readable storage device (125). Miniature medical sensors are available for portable applications. Such sensors are the subject of further miniaturization and cost reduction so as to be practical for application to the crime-scene body bag (100). Electronic noses that sniff out various medical conditions are known that can instantly analyze for the presence of certain chemicals. An example of one such bio-medical scanner (505) includes a micrometer-size sensor that relies on semiconductor technology to intensify tiny signals to readable levels. This capability allows for the reading of glucose concentration levels in a breath sample, which were previously thought to be too small to ensure accuracy. This chip-based sensor is reported to cost as little as 20 cents to manufacture.

The crime-scene body bag (100) may include a radiation dosimeter (520) that stores data on the non-transitory computer readable storage device (125). The radiation dosimeter (520) may be a radiation dosimeter badge, or preferably, the more modern thermoluminescent dosimeter.

The crime-scene body bag (100) may include a locking bar (525), which is a means to lock closed the zippering mechanism (115). Preferably, the locking bar (525) is a projection from the bag that can be interlaced with the pull tab on the zippering mechanism (115) so that a padlock can secure them together as shown in FIG. 5.

The crime-scene body bag (100) may include an end-lift handle (530) at an end of the bag. Preferably, there is an end-lift handle (530) at each end of the crime-scene body bag (100) to enable two people to pick-up and carry the crime-scene body bag (100).

The crime-scene body bag (100) may further include a central lifting strap (531) so that a crane or mechanical lifting device can pick-up and re-locate the crime-scene body bag (100).

The crime-scene body bag (100) may include a zippered pouch (515), which is used to store miscellaneous items outside the interior chamber (205) where the remains (215) are kept.

The crime-scene body bag (100) may include a vacuum attachment (510), which enables sucking out vapors and gaseous content from within the interior chamber (205). The gases can be simply discharged, routed to an incinerator, or directed to a gas chromatograph for analysis.

The above-described embodiments including the drawings are examples of the invention and merely provide illustrations of the invention. Other embodiments will be obvious to those skilled in the art. Thus, the scope of the invention is determined by the appended claims and their legal equivalents rather than by the examples given.

INDUSTRIAL APPLICABILITY

The invention has application to the storage bag industry.

What is claimed is:

1. A crime-scene body bag comprising:
a flexible material forming an enclosure, the enclosure defining an interior chamber having an axial length and a width sufficient to accommodate remains of a deceased person;
the enclosure comprising a zippering mechanism for opening and closing the enclosure, the zippering mechanism extending along the axial length of the enclosure to enable placement of the remains of the deceased person in the enclosure;
a platform embedded into the flexible material, the platform comprising;
a non-transitory computer readable storage device;
a fingerprint scanner able to store fingerprint data on the non-transitory computer readable storage device;
a digital voice recorder able to store audio entries as data on the non-transitory computer readable storage device;
a camera able to store images as data on the non-transitory computer readable storage device;
a nozzle communicating with the interior chamber of the bag to enable insertion of a cover gas, the nozzle further connected to a sensor that prevents cover gas insertion when the zippering mechanism is open, the nozzle comprising a release valve that releases gases within the enclosure when over-pressurization occurs;
a global positioning system monitor able to transfer location information from the global positioning system monitor to a requesting computer;
a screen that enables a user to view and access the data in the non-transitory computer readable storage device; and
a radio-frequency identification tag responsive to radio-frequency queries.

2. The crime-scene body bag of claim 1, further comprising a pressurized gas capsule attached to the platform, the pressurized gas capsule comprising the cover gas is connected to the nozzle so as to permit injection of the cover gas over the remains within the enclosure.

3. The crime-scene body bag of claim 1, further comprising an odor absorbing compound within the interior chamber.

4. The crime-scene body bag of claim 1, further comprising an anti-bacterial agent within the interior chamber.

5. The crime-scene body bag of claim 1, wherein the sensor is connected to the non-transitory computer readable storage device to record data identifying when the zippering mechanism is opened and the location of the crime-scene body bag when the zippering mechanism is opened.

6. The crime-scene body bag of claim 1, further comprising a bio-medical scanner that outputs data to the non-transitory computer readable storage device.

7. The crime-scene body bag of claim 1, further comprising a radiation dosimeter that stores data on the non-transitory computer readable storage device.

8. The crime-scene body bag of claim 1, further comprising a locking bar.

9. The crime-scene body bag of claim 1, further comprising an end-lift handle.

10. The crime-scene body bag of claim 1, further comprising a central lifting strap.

11. The crime-scene body bag of claim 1, further comprising a zippered pouch.

12. The crime-scene body bag of claim 1, further comprising a vacuum attachment.

* * * * *